US011037661B2

(12) United States Patent
Morris et al.

(10) Patent No.: US 11,037,661 B2
(45) Date of Patent: Jun. 15, 2021

(54) PATIENT-CENTRIC MODELING OF PATIENT DATA

(71) Applicant: Curesoft, Inc., San Francisco, CA (US)

(72) Inventors: Michael Morris, San Francisco, CA (US); Daniel Fobes, Yardley, PA (US)

(73) Assignee: CURESOFT, INC., San Francisco, CA (US)

( * ) Notice: Subject to any disclaimer, the term of this patent is extended or adjusted under 35 U.S.C. 154(b) by 259 days.

(21) Appl. No.: 15/604,537

(22) Filed: May 24, 2017

(65) Prior Publication Data

US 2017/0255697 A1    Sep. 7, 2017

(51) Int. Cl.
*G06F 16/30*    (2019.01)
*G16H 10/60*    (2018.01)
(52) U.S. Cl.
CPC ................... *G16H 10/60* (2018.01)
(58) Field of Classification Search
CPC .................................................. G16H 10/60
USPC .................................................. 707/700
See application file for complete search history.

(56) References Cited

U.S. PATENT DOCUMENTS

| 2006/0036395 | A1* | 2/2006 | Shaya | G01G 19/4146 |
| | | | | 702/127 |
| 2010/0222648 | A1* | 9/2010 | Tan | G16H 40/40 |
| | | | | 600/301 |
| 2015/0051922 | A1* | 2/2015 | Rentas | G06F 19/366 |
| | | | | 705/3 |
| 2015/0288797 | A1* | 10/2015 | Vincent | H04W 4/90 |
| | | | | 455/404.2 |
| 2016/0153041 | A1* | 6/2016 | Henderson | C12Q 1/6883 |
| | | | | 514/44 A |
| 2017/0011183 | A1* | 1/2017 | Valverde, Jr. | G06F 19/345 |

* cited by examiner

*Primary Examiner* — Anhtai V Tran
(74) *Attorney, Agent, or Firm* — Nicholson De Vos Webster & Elliott LLP

(57) ABSTRACT

Exemplary methods, apparatuses, and systems generate and maintain patient-specific models of patient data to assist in monitoring a patient's unique health conditions, and to provide more informative analyses of patient data and the relationships between elements of patient data. When a patient modeling server receives patient data from an external device, the patient modeling server determines whether values for elements of patient data satisfy individualized ranges for the elements of patient data, specific to the patient. In response to this determination, the patient modeling server can transmit notification and/or alert messages, and modify the individualized ranges for the elements of patient data. The patient modeling server also determines relationships between elements of patient data, based on analyses performed on the elements of patient data, to generate patient-specific models.

20 Claims, 6 Drawing Sheets

PATIENT-CENTRIC MODELING OF PATIENT DATA

FIELD OF THE INVENTION

The various embodiments described in this document relate to the management of patient data and generating patient-specific models of the patient data.

BACKGROUND OF THE INVENTION

When doctors diagnose patients with a condition, the doctors typically treat the condition by following standard treatment protocols. Treatment protocols guide the treatment and management of conditions by encouraging the use of treatments with proven benefits for a large population of patients and discouraging the use of ineffective treatments. However, while doctors design treatment protocols to improve the consistency of care across patients with the same condition, neither patients nor their conditions are identical. When a doctor applies the same treatment protocol for a condition to multiple patients, one patient's condition may improve, while another patient's condition worsens or does not change. For example, to treat cancers in patients, doctors are increasingly prescribing immunotherapy drugs. These immunotherapy treatments are new and work by stimulating the patient's immune system to aggressively attack cancer cells. In some situations, treating patients with immunotherapy drugs can have the desired effect as to the cancer itself. However, immunotherapy treatments can hyper stimulate the immune system to the point where the immune system begins attacking healthy cells and organs. In some situations, side effects of immunotherapy drugs may appear randomly and without any clear indications as being a result of the immunotherapy drugs. Because these treatments are new and often involve the combination of multiple treatments, doctors can be caught off guard by unexpected and unforeseen side effects and symptoms. For example, side effects of an immunotherapy drug that mimic test results indicative of a heart attack can lead to a misdiagnosis, while other side effects may go completely undiagnosed. The inability to recognize the full impact of immunotherapy drugs to a cancer patient and lack of knowledge as to which patients are susceptible to side effects, can result in severe consequences to the patient, including death.

Another issue that arises while treating a patient is that doctor visits and patient tests only provide a snapshot of the patient's condition. The patient's condition may worsen between tests and remain undetected until the patient notices significant symptoms. One approach to solving this deficiency is to regularly monitor or conduct tests on the patient to obtain more real-time data of a patient's condition. For example, a patient can use wearable devices that regularly monitor and gather information regarding the patient. In this approach, the wearable devices transmit the data to a system that uses a general model based on treatment protocols for the patient's condition. This, however, still suffers the drawbacks discussed above with respect to treatment protocols, as the general model is based on generalized knowledge of treatments related to the condition rather than the individual patient.

BRIEF DESCRIPTION OF THE DRAWINGS

The present invention is illustrated by way of example and not limitation in the figures of the accompanying drawings, in which like references indicate similar elements, and in which.

DETAILED DESCRIPTION

This document describes embodiments that implement a method of generating and maintaining patient-specific models of patient data. Embodiments generate and maintain the patient-specific models by receiving and analyzing data for a patient, determining individualized ranges for patient data collected for a patient, and using the individualized ranges and trends to anticipate, predict, or otherwise detect changes with respect to the patient's health or condition that may require a notification message or alert to the patient or a caregiver. To further enhance the patient-specific models, embodiments use the patient data to identify relationships between elements of patient data for a patient. In some embodiments, relationships may be unique or otherwise vary from patient to patient based on changes in values in patient data that are detected concurrently, within a number of samples of each other, or within an amount of time of each other. The process described herein solves the deficiencies of prior systems by efficiently tailoring the patient-specific model, including the ranges for elements of the patient data associated with the patient, and the relationships between elements of patient data, based on the patient's own data rather than a generalized model based on generalized knowledge of treatments for conditions.

Figure 1:
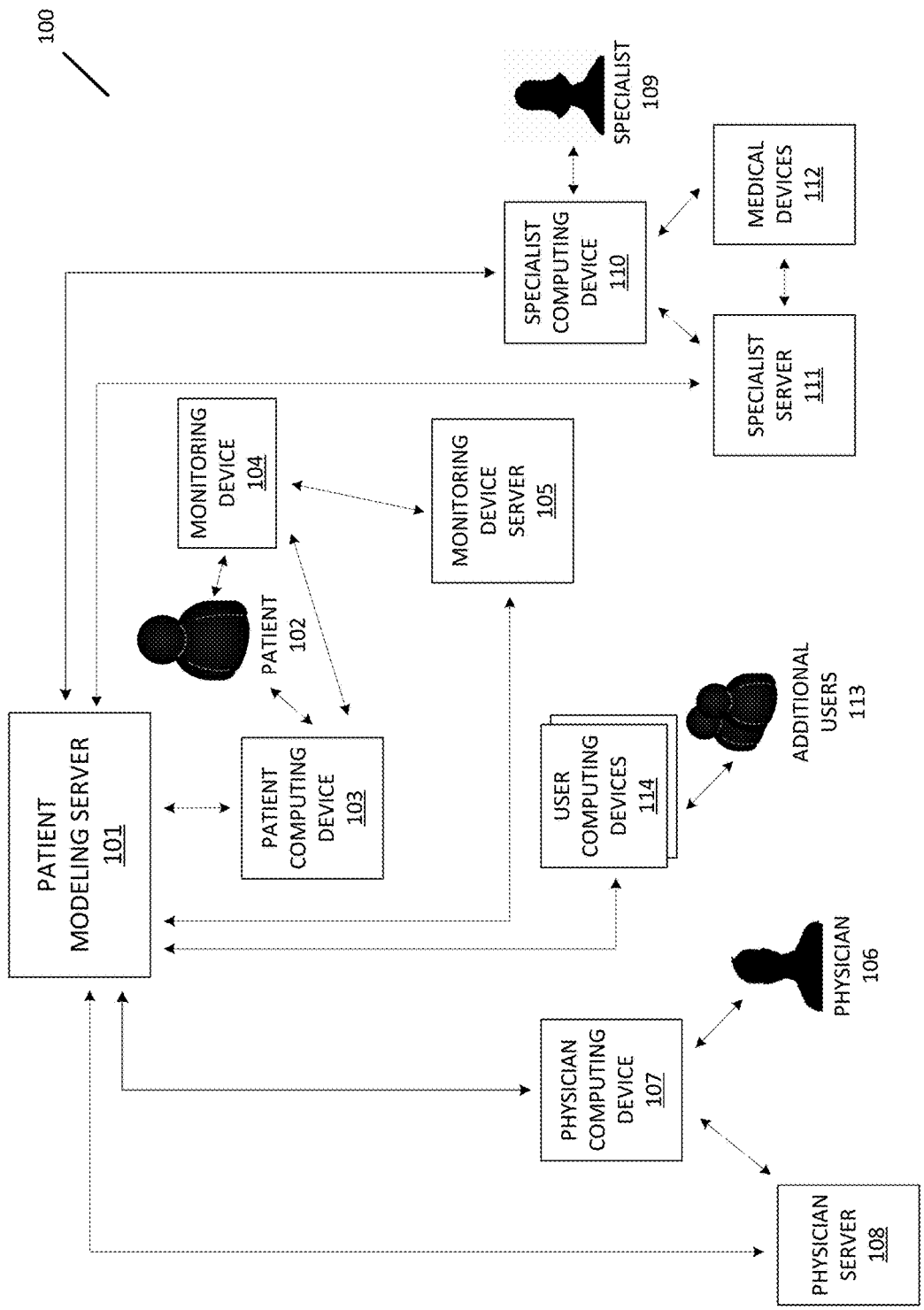
FIG. 1 illustrates an exemplary networked environment for generating, maintaining, and using patient-specific models of patient data.

FIG. 1 illustrates exemplary networked environment 100 for generating, maintaining, and using patient-specific models of patient data. Networked environment 100 includes patient modeling server 101, patient computing device 103 associated with patient 102, physician computing device 107 and physician server 108 associated with physician 106, specialist computing device 110 and specialist server 111 associated with specialist 109 and medical devices 112. Networked environment 100 also includes monitoring device 104, connected to monitoring device server 105, and configured to monitor patient 102 and gather and transmit patient data regarding patient 102. In one embodiment, networked environment 100 includes connections between patient modeling server 101 and user computing devices 114 associated with additional users 113 to maintain patient-specific models for additional users 113. In one embodiment, physician 106, specialist 109, and additional users 113, access patient modeling server 101 via physician computing device 107, specialist computing device 110, and user computing devices 114, respectively. In one embodiment, physician 106 and specialist 109, input patient data gathered by devices (e.g., stethoscope, thermometer, blood pressure monitor) via physician computing device 107, and specialist computing device 110, respectively. In addition, patient 102 can input patient data via patient computing device 103, including medications taken, dosages, and diet information.

Patient computing device 103, monitoring device server 105, physician computing device 107, physician server 108, specialist computing device 110, specialist server 111, and user computing devices 114 receive input as well as transmit and/or receive data via a network. Exemplary computing devices and servers that may serve as one or more of patient computing device 103, monitoring device server 105, physician computing device 107, physician server 108, specialist computing device 110, specialist server 111, and user computing devices 114 include a desktop or laptop computer, tablet computers, a server computer, or devices having computer functionalities such as Personal Digital Assistants (PDA), cellular or mobile telephones, smart-phones, in- or out-of-car navigation systems, gaming devices, or other electronic devices programmed to implement one or more embodiments set forth herein.

Exemplary monitoring devices 104 include devices housing data gathering and monitoring sensors, including sensors that gather biometric data (e.g., heart rate, brainwave, etc.), environmental data (temperature, altitude, etc.), and activity data (e.g., diet/nutritional data, exercise data, sleep data, etc.). Exemplary monitoring devices 104 include devices worn on, or otherwise attached to, a patient's body (e.g., wearable devices, fitness trackers, etc.) and devices that perform tests to gather patient data (e.g., glucose meter, thermometer, etc.). Monitoring devices 104 includes devices that are ingested by patient 102 or surgically implanted on or within patient 102. In one embodiment, monitoring device 104 monitors patient 102, gathers patient data, and sends the patient data to monitoring device server 105. In an alternate embodiment, monitoring device 104 sends the patient data to patient computing device 103 and patient computing device 103 forwards the patient data to monitoring device server 105 or to patient modeling server 101. In one embodiment, monitoring devices 104 communicate with and send data to computing devices and servers via wired or wireless connections (e.g., Wi-Fi, Bluetooth, etc.)

Exemplary medical devices 112 include devices that monitor patients and/or gather patient data (e.g., imaging, analyses, etc.). Exemplary medical devices 112 include sphygmomanometers, glucose meters, endoscopes, X-ray generating devices, ultrasound devices, CT scanners, magnetic resonance imaging (MRI) devices, etc. In one embodiment, medical devices 112 send patient data to specialist server 111. In an alternate embodiment, medical devices 112 send the patient data to specialist computing device 110 and specialist computing device 110 forwards the patient data to specialist server 111 or to patient modeling server 101.

In one embodiment, patient computing device 103, monitoring device server 105, physician computing device 107, physician server 108, specialist computing device 110, specialist server 111, and user computing devices 114 interface and interact with patient modeling server 101. For example, a medical practitioner using physician computing device 107 or specialist computing device may enter the notes on or the results of a biopsy, scan or image results, a blood panel, genetic test, etc. In one embodiment, an application stored on patient computing device 103 interacts with patient modeling server 101 to transmit patient data to patient modeling server 101 and/or to access patient-specific models, as described with reference to FIGS. 3-6. For example, the application may be a web browser application (e.g., Microsoft Windows Internet Explorer, Mozilla Firefox, Apple Safari, Google Chrome, Opera, etc.). In one embodiment, the application is a special-purpose client application. For example, the application may be a part of the native platform or operating system of the computing device or server, such as Windows®, Mac OSX®, iOS®, or ANDROID™, which may utilize an Application Programming Interface (API) to directly interface with patient modeling server 101 through API request server 122.

Patient computing device 103, monitoring device server 105, physician computing device 107, physician server 108, specialist computing device 110, specialist server 111, and user computing devices 114 are configured to communicate with patient modeling server 101 via a network or a collection of networks—such as the Internet, a corporate intranet, a Virtual Private Network (VPN), a Local Area Network (LAN), a Wireless Local Area Network (WLAN), a cellular network, a Wide Area Network (WAN), a Metropolitan Area Network (MAN), or a combination of two or more such networks. The network may be wired, wireless, or a combination of both. In one embodiment, the network uses standard communications technologies and/or protocols. Thus, the network may include links using technologies such as Ethernet, Institute of Electrical and Electronics Engineers (IEEE) 802.11, Worldwide Interoperability for Microwave Access (WiMAX), 3G, 4G, Long Term Evolution (LTE), Code-Division Multiple Access (CDMA), Digital Subscriber Line (DSL), cable modems, etc. Similarly, the networking protocols used on network 110 may include Multiprotocol Label Switching (MPLS), Transmission Control Protocol (TCP), Internet Protocol (IP), TCP/IP, User Datagram Protocol (UDP), Hypertext Transport Protocol (HTTP), Simple Mail Transfer Protocol (SMTP), and/or File Transfer Protocol (FTP). Data exchanged over network 110 may be represented using technologies and/or formats including Hypertext Markup Language (HTML), Extensible Markup Language (XML), or JavaScript Object Notation (JSON), among other formats. In addition, all or some of links can be encrypted using conventional encryption technologies such as Secure Sockets Layer (SSL), Transport Layer Security (TLS), or Internet Protocol security (IPsec), and can employ two-factor or multi-factor authentication for access control.

Figure 2:
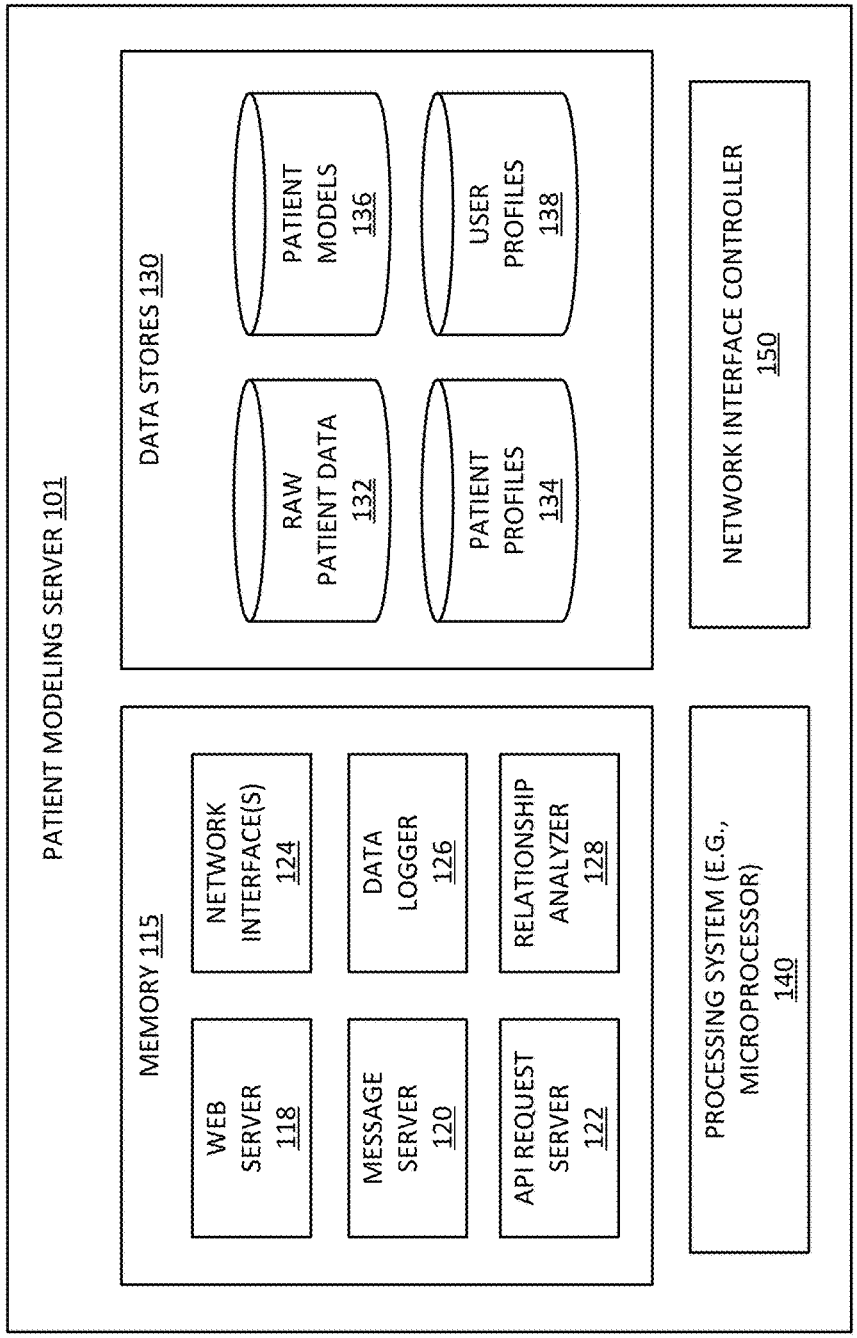
FIG. 2 illustrates, in block diagram form, an exemplary patient modeling server.

Patient modeling server 101, as described with reference to FIG. 2, includes memory 115, data stores 130, processing system 140, and network interface controller (NIC) 150. In this embodiment, memory 115 stores modules including web server 118, message server 120, API request server 122, network interface(s) 124, data logger 126, and relationship analyzer 128. This embodiment includes, within data stores 130, raw patient data data store 132, patient profiles data store 134, patient models data store 136, and user profiles data store 138. Memory 115 and data stores 130 can be one or more of volatile memory (e.g., DRAM) and nonvolatile memory (e.g., flash memory, a hard drive, and Phase-Change Memory (PCM)). In other embodiments, patient modeling server 101 includes additional, fewer, or different modules for various applications. In one embodiment, processing system 140 retrieves instruction(s) from the memory 115, and executes the instructions to perform operations described herein. NIC 150 facilitates network connections between patient modeling server 101 and other computing devices (e.g., patient computing device 103) and servers (e.g., physician server 108) by connecting patient modeling 101 to a network. In embodiments, NIC 150 facilitates communications using a wired connection (e.g., Ethernet) and/or a wireless connection (e.g., Wi-Fi, Bluetooth, etc.).

Patient modeling server 101 stores raw patient data in raw patient data data store 132. Patient data includes diagnostic information regarding patient 102, including measured data, test results, treatment information, etc. One or more of patient 102, monitoring device 104, physician 106, specialist 109, and/or medical devices 112 obtain or gather patient data, and patient modeling server 101 receives the patient data.

As patient modeling server 101 receives patient data from external sources, including patient computing device 103, monitoring device server 105, physician computing device 107, physician server 108, specialist computing device 110, specialist server 111, and user computing devices 114, patient modeling server 101 stores the received data in raw patient data data store 132. In one embodiment, patient modeling server 101 determines a patient associated with received patient data using patient identifying information (e.g., name, patient identifier, etc.) included with the received raw patient data. In one embodiment, raw patient data data store 132 stores structured data (e.g., numeric data and/or alphanumeric data) and unstructured data (e.g., scans/x-rays and scan results). In other embodiments, raw patient data data store 132 stores textual data of the patient, and multimedia stores associated with the patient store the unstructured data (e.g., images, videos, etc.) by associating a patient identifier with an identifier of the unstructured data. In one embodiment, patient modeling server 101 stores the raw patient data in a raw patient data table that stores patient data for the corresponding patient, as described with reference to FIG. 3. In such embodiments, patient modeling server 101 determines or utilizes a patient identifier to retrieve a raw patient data table for the specific patient from raw patient data data store 132. In one embodiment, raw patient data data store 132 stores patient data specific to one or more patients, one or more conditions, a specific physician, or specialist.

In one embodiment, patient modeling server 101 stores treatment data in raw patient data data store 132 to track the effects of treatments on physical attributes, treatments, and/or test results. For example, patient modeling server 101 can track the effects of medications prescribed to patient 102, or track the effects of an immunotherapy treatment for cancer, on physical attributes, treatments, and/or test results. Similarly, patient modeling server 101 can compare chemotherapy treatment data (e.g., dosage, duration) with the effectiveness on tumor growth or shrinkage. To that end, raw patient data data store 132 can include a treatments table tracking patient data for sleep, steps/activities, medications, etc. In one embodiment, the treatments table includes columns for: treatment name, treatment identifier, treatment value (e.g. hours (sleep), number of steps (exercise), calories (diet), and dosage (medication)), start date, and start time. In one embodiment, a raw patient data table can be extended to include the patient data from the treatments table, as described above.

Patient modeling server 101 stores patient profiles in patient profiles data store 134. Each patient profile in patient profiles data store 134 includes information about the corresponding patient, including information shared by the patient, and information about the patient received from external sources (e.g., monitoring device server 105, physician server 108, and specialist server 111), including textual data and multimedia content. A patient profile includes multiple data fields, each data field describing one or more attributes of the corresponding patient. In one embodiment, each patient profile includes patient identifying information (e.g., name, patient identifier, etc.). The patient profile information stored in patient profile data store 134 describes patient 102 (and additional users 113) of patient modeling server 101, including biographic, demographic, medical, family history, and other types of descriptive information, such as race, gender, height/weight, and location. Patient profiles data store 134 also stores information regarding medications assigned to patient 102, including refill rates, dosage amounts, timing of dose, and adherence to the medications. Patient profile data store 134 also stores patient data that may not be tied to a specific physical attribute or other element of patient data for patient 102, including patient data related to diet/nutrition (e.g., caloric intake), exercise (e.g., number of steps taken daily, number of active minutes, etc.), lifestyle (e.g., smoking, drinking, etc.), and sleep (e.g., number of hours a patient sleeps, sleep analysis data, etc.).

Patient modeling server 101 also stores mapping tables in patient profiles data store 134. Patient modeling server 101 uses mapping tables to correlate received raw patient data stored in raw patient data data store 132 with ontology object identifiers (e.g., nodes) to generate the ontological data structure, e.g., as described with reference to FIG. 3.

Patient modeling server 101 stores patient models in patient models data store 136. In one embodiment, patient modeling server 101 generates the patient models as ontological data structures comprising visual representations (e.g., nodes) of elements of patient data associated with patient 102. The ontological data structures also include visual representations indicating relationships between the elements of patient data, including individualized relationships determined from the patient data for patient 102. Nodes can represent physical attributes. Examples of physical attributes of patient 102 include regions of the body (e.g., arms, chest, head), organs (e.g., heart, liver, kidneys), and other components of the body (e.g., blood). Each element of patient data can be associated with specific physical attributes of patient 102. In addition to physical attributes, nodes can be used to represent individual tests, measurements and treatments, without being tied to a specific physical attribute. For example, a patient model can include nodes for blood pressure, glucose levels. In one embodiment, the ontological data structures also include nodes representing other patient data, e.g., including treatment data, medication data, diet/nutrition data, exercise data, and sleep data. In such embodiments, patient models data store 136 also stores visual representations (e.g., edges) indicating relationships between these additional nodes and with nodes representing elements of patient data.

In one embodiment, patient modeling server 101 stores, or otherwise associates, patient data with one or more associated nodes. For example, patient modeling server 101 associates patient data in the form of blood pressure readings with the heart. In one embodiment, patient modeling server 101 stores patient data for each node (or as applicable) in patient models data store 136. In one embodiment, the patient data stored in patient models data store 136 is a subset of the patient data stored in raw patient data data store 132 or data generated from the patient data stored in raw patient data data store 132. For example, patient modeling server 101 stores minimum values and maximum values representing an individualized range for the patient, historical values, and average values for each element of patient data represented by a node in patient models data store 136. Patient models data store 136 also stores visual data (e.g., x-rays, scans, and ultrasounds) for elements of patient data represented by nodes. In other embodiments, patient models data store 136 includes a mapping table with pointers to raw patient data data store 132 linking an ontology object with the patient data for the ontology object. In one embodiment, patient models data store 136 stores the most recent data for each node, while raw patient data data store 132 stores all of the data for each node.

User profiles data store 138 stores profiles for users accessing patient modeling server 101. In one embodiment, each user profile includes user credentials usable by patient modeling server 101 to identify whether the user is patient 102, physician 106, specialist 109, or one of additional users 113. In one embodiment, patient modeling server 101 provides different default views of the ontological data structure representing patient 102 based on the user, as determined by the user credentials, accessing patient modeling server 101. For example, patient modeling server 101 can provide a more generalized ontological data structure containing a complete or full view of patient data to patient computing device 103 when the requesting user is patient 102, and provide a specific subset of the ontological data structure to specialist computing device 110 when the requesting user is specialist 109. In one embodiment, patient modeling server 101 provides the specific subset based on the type of specialization for specialist 109 (e.g., a default ontological data structure for oncologists).

In one embodiment, patient modeling server 101 stores permission or access information in the user profiles to maintain and enforce permissions associated with user credentials. For example, patient 102 can allow limited access to the patient data or ontological data structure to one user, while allowing greater or full access to another user. In such embodiments, patient modeling server 101 queries user profiles data store 138 to determine permissions associated with the user credentials. Patient modeling server 101 grants the user access to the data stored at patient modeling server 101, including a user profile and a user's ontological data structure in response to determining the permissions associated with the user credentials grant access to the patient modeling server 101.

Web server 118 links patient modeling server 101 via a network to one or more devices (e.g., patient computing device 103) and servers (e.g., monitoring device server 105) by accepting requests from devices and servers and/or transmitting web pages or other web-related content to devices and servers, such as image files, audio files, video files, Java applets, Flash, XML, JavaScript, Cascading Style Sheets (CSS), and so forth. Web server 118 in some embodiments utilizes a set of one or more network interfaces 124 to send and receive messages across a network. In some embodiments, web server 118 (additionally or alternately) utilizes message server 120 (e.g., a dedicated server end station, a dedicated software application, etc.) to communicate with devices and servers. In such embodiments, message server 120 is operative to send and/or receive instant messages, queued messages (e.g., email), text and SMS (Short Message Service) messages, or utilize any other suitable messaging technique. In one embodiment, message server 120 sends and receives secure or encrypted messages. In addition, message server 120 is operative to send alert messages, e.g., in response to a given value of patient data crossing a threshold or changing by greater than a predetermined amount.

API request server 122 allows external systems (e.g., patient computing device 103, physician server 108) to access information from or transmit information to patient modeling server 101 by issuing API calls. In one embodiment, patient modeling server 101 provides access to patient data, including to ontological data structures generated by patient modeling server 101 based on the patient data received for a particular patient. For example, physician 106, using physician computing device 107, accesses patient modeling server 101 to view the ontological data structure, or subset of the ontological data structure, for patient 102, for monitoring or diagnostic purposes. In addition, physician 106 accesses patient modeling server 101 to view the raw patient data to obtain patient data (e.g., hospitalization history, history of condition, previous treatments/medications) and for patient analysis. Patient modeling server 101 receives API requests via API request server 122, and patient modeling server 101 then processes the request by performing actions sought by the API requests, determining appropriate responses to the API requests, and transmitting back these responses back to the requesting device or server.

Network interfaces 124 include NIC drivers to allow NIC 150 to establish network connections between patient modeling server 101 and other computing devices (e.g., patient computing device 103) and servers (e.g., physician server 108) by connecting patient modeling 101 to a network.

When patient modeling server 101 receives patient data, data logger 126 records the patient data to raw patient data data store 132 by processing the patient data to the appropriate patient profile in raw patient data data store 132. For example, data logger 126 identifies the raw patient data as being for patient 102 by determining a patient identifier included in the patient data matches the patient profile for patient 102. In one embodiment, after data logger 126 determines the appropriate patient profile, data logger 126 stores the received patient data in the raw patient data table associated with the patient profile. For example, data logger 126 determines and enters the data for each data field in the raw patient data table.

Relationship analyzer 128 analyzes patient data received from patient computing device 103, monitoring device server 105, physician server 108, and specialist server 111, to maintain and determine relationships between nodes (e.g., physical attributes, treatments, test results). For example, relationship analyzer 128 analyzes data regarding pre-established relationships between nodes, as well as analyzes data to identify potential new relationships between nodes. In one embodiment, relationship analyzer 128 establishes or maintains a relationship between data values for two nodes when changes in values for one node impacts or is impacted by changes in values for another node. For example, a node representing a heart has a relationship with heart rate because the heart rate has an impact on the functioning of the heart. In one embodiment, relationship analyzer 128 determines two nodes have a relationship based on changes in data regarding the two nodes. In such embodiments, relationship analyzer 128 detects a change in a value for an element of patient data associated with a first node and a change in value for an element of patient data associated with a second node, and determines that the first node and the second node have a relationship because of the changes in values for the first node and the second node. Relationship analyzer 128 can determine relationships between two physical attributes of a patient, as well as between patient profile data and a physical attribute of the patient. For example, relationship analyzer 128 can determine a relationship when a change in dosage in a medication used by a patient can be linked to a change in value with a physical attribute of the patient. In another example, when a node for exercise data includes information regarding the number of steps patient 102 takes daily, relationship analyzer 128 can determine if relationships exist between an increase (or decrease) in the number of steps patient 102 takes and sucrose levels in a diabetic patient.

In one embodiment, relationship analyzer 128 evaluates changes in values over a period, and determines a change in value of the physical attribute associated with the second node that occurs within a short period from a change in value of the physical attribute associated with the first node is more likely to indicate a relationship than changes that occur with a greater time separation. Relationship analyzer 128 also establishes a relationship between data values for two nodes when a first physical attribute represented by a first node is a part of or otherwise contained within a second physical attribute represented by a second node. For example, the node representing the heart also has relationships with components of the heart (e.g., chambers, blood vessels, aorta, etc.). An exemplary method of maintaining relationships between nodes in an ontological data structure is described in greater detail with reference to FIG. 5. In one embodiment, by evaluating patient data for patient 102 to detect relationships and evaluate relationships that may be unique to patient 102, patient modeling server 101 can detect and evaluate patient-specific effects of treatments to physical attributes (or other elements associated with patient data) and other test results of patient 102, including effects that may not be derivable from evaluating the patient data in isolation.

In one embodiment, patient modeling server 101 uses the patient data and associated relationships to generate the ontological data structure, including subsets (e.g., filtered views) based on conditions and relationships. For example, patient modeling server 101 maintains a default ontological data structure that includes all nodes. When a user requests patient modeling server 101 to display a filtered view representing a subset of the ontological data structure, patient modeling server 101 displays the filtered view by displaying the subset of the ontological data structure that includes the desired nodes, including any nodes that have a relationship with the nodes. In one embodiment, in response to a request to view a patient ontology related to liver cancer, patient modeling server 101 displays a default filtered view for liver cancer, including a node representing a liver, and any nodes having a relationship with the liver. In such embodiments, the default filtered view is configurable based on user preferences and/or based on determined relationships between nodes, to include or exclude additional nodes.

In one embodiment, relationship analyzer 128 compares ontological data structures of different patients. For example, relationship analyzer 128 compares a first ontological data structure of a first patient with a second ontological data structure of a second patient. In some embodiments, relationship analyzer 128 compares the first and second ontological data structures when the first patient and the second patient have a similar or same condition. In other embodiments, relationship analyzer 128 compares the first and second ontological data structures based on other factors, e.g., similar demographics of the first patient and the second patient. By comparing ontological data structures, relationship analyzer 128 can determine differences between nodes and relationships included in each ontological data structure for patients with the same condition and/or other similarities. In one example, relationship analyzer 128 determines that the second ontological data structure includes a relationship in addition to the relationships included the first ontological data structure. In one embodiment, in response to this determination, patient modeling server 101 modifies the first ontological data structure to include the relationship. In some embodiments, patient modeling server 101 requests additional patient data, including new inputs, in response to the creation of the new relationship in the first ontological data structure. In one embodiment, patient modeling server 101 requests additional patient data to determine if the same relationship may exist for the first patient prior to modifying the first ontological data structure to include the relationship. In other embodiments, relationship analyzer 128 evaluates additional ontological data structures of other patients to determine if the relationship is a general relationship that can be applied to other ontological data structures, or if the relationship is specific to the second patient.

In another example, relationship analyzer 128 evaluates a patient pool having similar profiles (e.g., based on demographics, condition, treatments, etc.) to determine causes of variations in results from treatments. For example, all patients in a patient pool may be treated with the same immunotherapy treatment for liver cancer, but only patients in a subset have shown improvements in their conditions. In such examples, relationship analyzer 128 can evaluate the elements of patient data over the duration of the treatment, in addition to relationships between elements of patient data, to determine factors or patient-specific information that may indicate why the subset of the patient pool experiences better outcomes from the treatment versus other patients in the patient pool.

It will be apparent from this description that aspects of the inventions may be embodied, at least in part, in software. That is, computer-implemented methods 400, 500, and 600, may be carried out in a computer system or other data processing system, such as patient modeling server 101, in response to its processor executing sequences of instructions contained in a memory or another non-transitory machine-readable storage medium. The software may further be transmitted or received over a network (not shown) via a network interface. In various embodiments, hardwired circuitry may be used in combination with the software instructions to implement the present embodiments. It will also be appreciated that additional components, not shown, may also be part of patient modeling server 101, and, in some embodiments, fewer components than that shown in FIG. 2 may also be used in patient modeling server 101.

Figure 3:
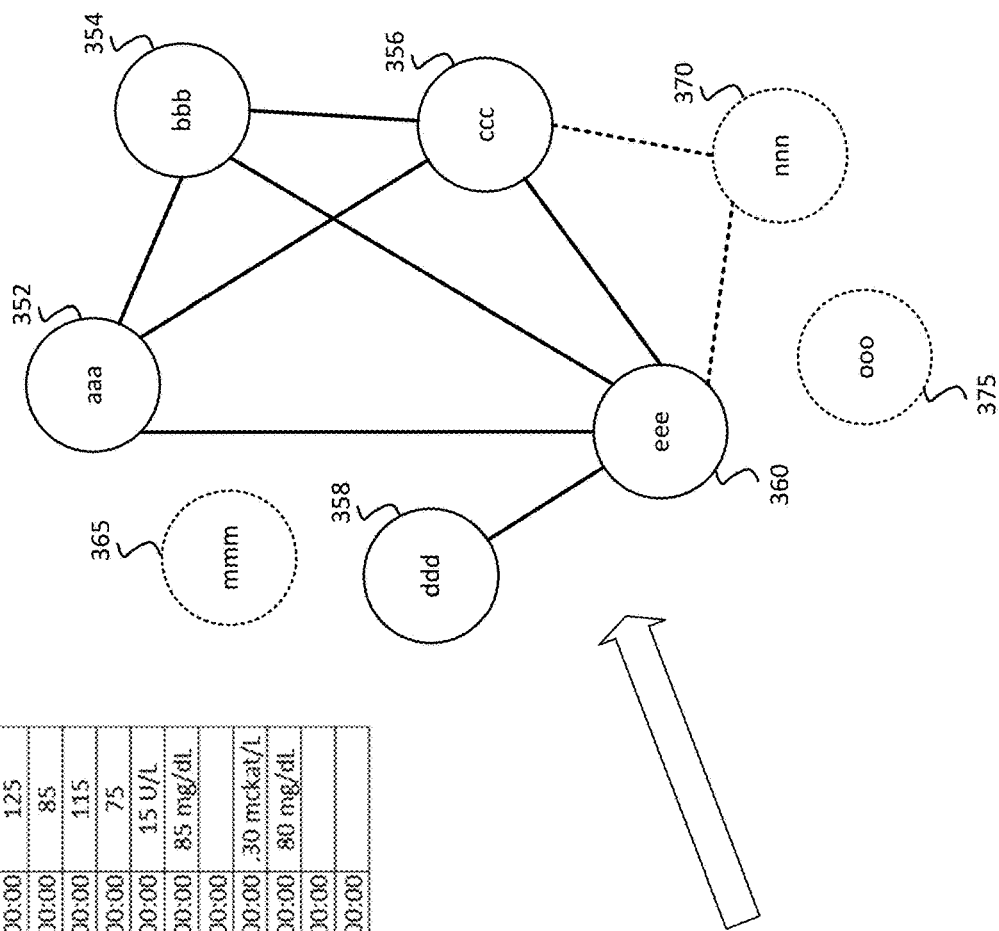
FIG. 3 illustrates an exemplary data structures storing patient data useful in a process for generating an ontological data structure.

FIG. 3 illustrates exemplary data structures storing patient data useful in a process for generating an ontological data structure 350. FIG. 3 includes raw patient data table 310, ontological mapping table 330, and an ontological data structure representing patient data in the form of patient ontology 350. In one embodiment, patient modeling server 101 receives raw patient data from one or more of patient computing device 103, monitoring device server 105, physician server 108, and specialist server 111. Patient modeling server 101 stores the raw patient data in raw patient data data store 132. In one embodiment, patient modeling server 101 receives the raw patient data in a known data format and/or parses the received raw patient data to identify fields and corresponding values. For example, patient modeling server 101 identifies test component identifiers associated with items in the raw patient data. When patient modeling server 10 detects a value in the raw patient data without a test component identifier or without a test component identifier known to patient modeling server 101, patient modeling server 101 assigns a temporary test component identifier. In this situation, patient modeling server 101 may send a message to a user (e.g., patient 102, physician 106, and specialist 109) requesting information regarding the value, including a physical attribute associated with the value. After identifying the values for the patient data, patient modeling server 101 enters the data into raw patient data data store 132.

Patient modeling server 101 utilizes data logger 126 to process the raw patient data into raw patient data data store 132 for storage in raw patient data table 310. The raw patient data includes a patient identifier (e.g., name, patient number, etc.) to allow data logger 126 to map the raw patient data to the appropriate patient profile in raw patient data data store 132. Patient modeling server 101 accesses the patient profile associated with the patient identifier to retrieve or modify the corresponding raw patient data table. For example, patient modeling server 101 receives blood pressure (BP) data from patient computing device 103 on Apr. 23, 2017 and Apr. 24, 2017, complete metabolic panel (CMP) data from physician server 108 on Sep. 1, 2016 and Apr. 30, 2017, and computerized tomography (CT) scan data from specialist server 111 on Jun. 1, 2017, and inputs the values into raw patient data table 310. In some scenarios, patient modeling server 101 receives duplicate data from multiple entities and identifies duplicate data based on date and time values and/or recognizes duplicate value readings. In such situations, patient modeling server 101 stores one set of the data and not duplicate data in raw patient data table 310.

In the depicted example, raw patient data table 310 includes test type, test component type, test component identifier (TestComponentId), date, time, and test value. In other embodiments, raw patient data table 310 includes additional or fewer data points. Patient modeling server 101 assigns test component identifiers to each unique patient data type. For example, in raw patient data table 310, patient modeling server 101 assigns systolic BP values TestComponentId "111," diastolic BP values TestComponentId "222," aspartate aminotransferase (AST) values TestComponentId "333," glucose values TestComponentId "444," and liver CT scans TestComponentId "555." In other embodiments, sources of the patient data (e.g., labs, doctors, etc.) assign the test component identifiers and patient modeling server 101 uses the received test component identifiers. In other embodiments, patient modeling server 101 uses industry standard identifiers for the test components.

Patient modeling server 101 uses the patient data in raw patient data table 310 to generate, or otherwise supplement, ontological mapping table 330. For example, ontological mapping table 330 can include a set of default mappings that are included for all patients, and modified as patient data is received and analyzed. Patient modeling server 101 assigns an ontology object identifier (OntologyObjectId) to each TestComponentId by mapping a unique ontology object identifier to each type of element of patient data in ontological mapping table 330. For example, patient modeling server 101 assigns OntologyObjectId "aaa" to a node representing values of systolic BP, "bbb" to a node representing values of diastolic" BP, etc. Patient modeling server 101 uses ontology object identifiers to identify nodes within an ontological data structure.

When patient modeling server 101 updates raw patient data table 310 with additional patient data, patient modeling server 101 also maps the incoming values to the corresponding ontology object identifier based on ontological mapping table 330. For example, when patient modeling server 101 receives a new value for glucose level (Test Component Id="444") in raw patient data table 310, patient modeling server 101 maps the new value to OntologyObjectId "ddd." In embodiments, patient modeling server 101 includes a pointer to an entry in raw patient data table 310 for the new glucose level and/or stores the new value in data structure associated with OntologyObjectId "ddd." In such embodiments, patient modeling server 101 uses a patient identifier associated with the patient to access the appropriate data in raw patient data table 310.

Patient ontology 350 illustrates one depiction of the ontological data structure. In other embodiments, patient modeling server 101 stores the ontological data structure in a table format. For example, ontological mapping table 330 can include additional columns that include, pointer entries for each ontology object identifier to indicate existing relationships with other ontology objects (e.g., nodes).

Patient modeling server 101 generates patient ontology 350 using the data from raw patient data table 310 and ontological mapping table 330. Based on the stored patient data about users, elements of patient data (e.g., physical attributes, treatments, etc.), and the connections between the users and/or elements of patient data, patient modeling server 101 generates and maintains patient ontology 350 in patient models data store 136. In patient ontology 350, elements of patient data are illustrated as circles (e.g., nodes) and relationships are illustrated as connections (e.g., edges) between circles.

In one embodiment, patient modeling server 101 generates a default set of nodes and relationships between nodes based on default settings or configurations. For example, patient modeling server 101 pre-loads each ontology with a default set of nodes and relationships prior to the patient modeling server 101 receiving patient data. Alternatively, or additionally, patient modeling server 101 determines the nodes and the relationships for a particular patient dynamically as patient modeling server 101 receives patient data. For example, as patient modeling server 101 receives additional patient data, patient modeling server 101, adds, removes, or otherwise modifies edges connecting the various nodes to reflect changes in relationship determined from the patient data. For example, when patient modeling server 101 determines a new relationship between two nodes, patient modeling server 101 creates and edge between the two nodes to indicate the relationship, and when patient modeling server 101 determines a relationship is no longer present, patient modeling server 101 removes the edge. In one embodiment, the addition and/or deletion of relationships between nodes is based on analyzing patient data over time and/or using a predefined number of samples (e.g., previous five test results), to determine patterns, or lack thereof, in the values of different nodes.

In one embodiment, relationships may be one-directional or bi-directional, depending on the patient data and the relationships derived from the patient data. For example, while received patient data may indicate a relationship where a change in values for a first node results in a change in values for a second node, the reverse relationship either may not exist or may not be determined until subsequent patient data is received and analyzed. In one embodiment, one-directional or bi-directional relationships between nodes are represented by edges with arrows indicating the determined directional relationship. In the above example, the patient modeling server 101 designates the first node as a source node, and the second node as a target node, to indicate the one-directional relationship. Alternatively, the patient modeling server 101 designates the first node as an "impacts" node, and the second node as an "impacted by" node. For example, a node related to a medication prescribed to patient 102 to lower sucrose levels of patient 102 can be designated as an "impacts" node, while a node for sucrose levels can be designated as an "impacted by" node. In one embodiment, a node can be both an impacts node and an impacted by node relative to different nodes.

In FIG. 3, nodes (i.e., aaa 352, bbb 354, ccc 356, ddd 358, eee 360, mmm 365, nnn 370, and ooo 375) and the relationships indicated in patient ontology 350 using solid lines (e.g., between node aaa 352 and node bbb 354) indicate default or previously-determined relationships. For example, node ddd 358, representing glucose level has a relationship with node eee 360, representing liver, because glucose levels have an impact on the functioning of the human liver. The relationships indicated using dashed lines indicate new relationships determined based on patient data for the particular patient. For example, patient modeling server 101 determines there is a relationship between node ccc 356 and node nnn 370 when a change in a value for node ccc 356 appears to affect the value in node nnn 370. The determination of such a relationship is described further with reference to FIG. 5. In this example, because node 356 has a relationship with node eee 360, patient modeling server 101 determines that a relationship also exists between node nnn 370 and node eee 360. Alternatively, patient modeling server 101 does not imply a relationship between node nnn 370 and node eee 360 based upon a determined relationship between node ccc 356 and node nnn 370 and, instead, evaluates each relationship independently and directly. In either case, the relationship indicated using the dashed lines may be personalized to the particular patient, and may not exist, by default or by observation, in other ontologies for other patients. In patient ontology 350, no relationship exists between nodes mmm 365 or ooo 375 and any of the other depicted nodes. However, in ontologies for other patients, patient modeling server 101 may determine that individualized relationships exist based on the patient data received for the other patients.

Figure 4:
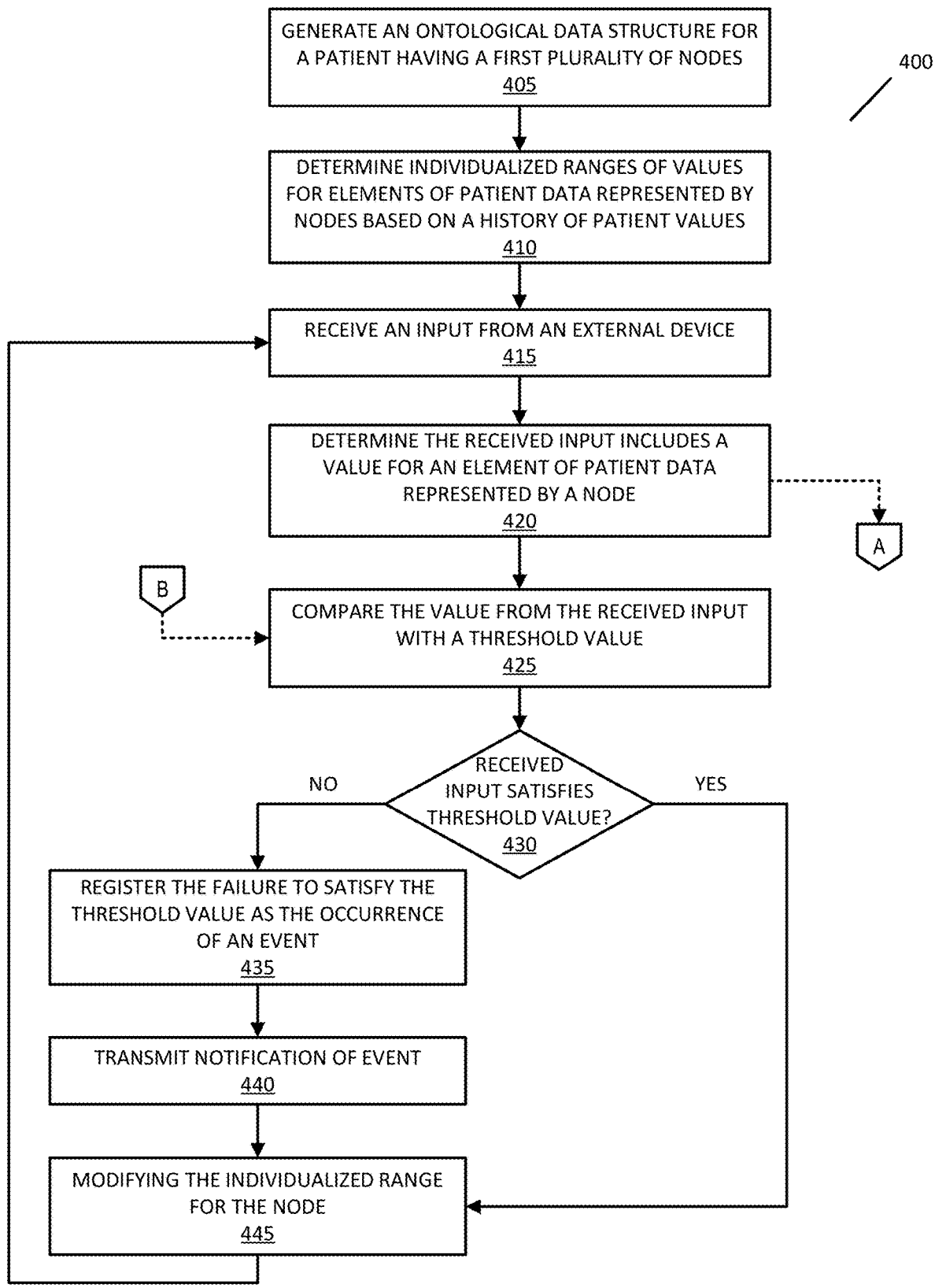
FIG. 4 is a flow chart illustrating an exemplary method for maintaining a patient-specific model of patient data using a patient modeling server.

FIG. 4 is a flow chart 400 illustrating an exemplary method for maintaining a patient-specific model of patient data using patient modeling server 101.

At block 405, patient modeling server 101 generates an ontological data structure for patient 102. In one embodiment, the ontological data structure is a graph that includes a plurality of nodes, where each node represents an element of patient data associated with patient 102. In one embodiment, elements of patient data may include, but are not limited to: a physical attribute of the patient, a test result of the patient, measured data of the patient, and a treatment applied to the patient.

In one embodiment, the ontological data structure includes edges connecting nodes, where the edges between two nodes indicates a relationship between the two connected nodes. In one embodiment, to indicate a one-directional relationship, an edge created between two nodes indicates one node as a source node and the other node as the target node, while in a bi-directional relationship, an edge created between two nodes indicates both nodes as sources and targets. Patient modeling server 101 generates the ontological data structure with a default set of nodes and edges, and stores the ontological data structure in patient models data store 136. For example, a default set of nodes for a patient can include nodes for the major organs of the body, nodes for components of standard blood tests, edges between the major organs that are related, and edges between the components of standard blood test and each of the major organs closely associated with the components of the standard blood tests. In another example, a default set of nodes and edges can include a node for a medication for treating diabetes with an edge to a node for blood test value of sucrose with an edge to nodes for pancreas and liver.

Patient modeling server 101 maintains values for the elements of patient data represented by the nodes and the edges connecting nodes indicate a relationship between the values of the connected nodes. The ontological data structure can be represented using other data structures. For example, the ontological data structure can be a table of data with relationships maintained using pointers between table entries.

At block 410, patient modeling server 101 determines individualized ranges of values for elements of patient data represented by nodes within the plurality of nodes using a history of values for patient 102. For example, patient modeling server 101 receives patient data from patient computing device 103, physician server 108, and/or specialist server 111. Patient modeling server 101 uses the received patient data to determine an individualized range of values for each element of patient data. In one embodiment, patient modeling server 101 determines the individualized range of values for a particular element of patient data based on: (1) the patient's own history of values for the particular element of patient data; (2) standardized values (e.g., a medically-determined range) for a healthy patient; (3) standardized values for other patients having a same condition as the patient; or (4) a combination of the preceding values. For example, the standard range for estimated glomerular filtration rate (eGFR), used to measure kidney health, includes values greater than 59 mL. Given values for eGFR for patient 102 of 95 mL, 84 mL, 110 mL, and 107 mL, from the previous four tests performed, patient modeling server 101 may determine an individualized range for patient 102 as being values between 84 mL and 110 mL. In another example, patient modeling server 101 calculates a standard deviation of the values from patient data.

In one embodiment, patient modeling server 101 determines a range of values based on the trends identified in the patient's own history of values for a specific or limited period. For example, patient modeling server 101 evaluates the patient's values over a predetermined amount of time (e.g., the previous four years), beginning at a specified time (e.g., date of diagnosis of a condition), or based on a specified number of test results. Patient modeling server 101 can further filter patient values based on other factor, including time. For example, range of values for an element of patient data can be based on the time the patient data was obtained because time of day can influence some test values the test is performed (e.g., blood pressure is typically lower in the morning).

In one embodiment, the range of values for an element of patient data is a set of values between an upper threshold and a lower threshold. For example, the standard range of values for fasting blood glucose level is between 70 and 99 mg/dL. Alternatively, or additionally, the range of values for another element of patient data can have either an upper threshold or a lower threshold, with the standard range of values is below the upper threshold or above the lower threshold, respectively. For other elements of patient data, the range of values is an amount of change, where the maximum or minimum amount of change is a threshold value. For example, the standard range for HDL cholesterol includes values greater than 39 mg/dL, and if patient 102 has a most recent value of 45 mg/dL, a user (e.g., physician 107) can set the maximum amount of change to −6 mg/dL, and any change greater than −6 mg/dL would trigger an alert or notification because the value would be outside the standard range.

At block 415, patient modeling server 101 receives an input from an external device. For example, patient modeling server 101 receives data from monitoring device server 105 of patient data generated by monitoring device 104.

At block 420, patient modeling server 101 determines that the received input includes a value for an element of patient data represented by a node in the plurality of nodes. Patient modeling server 101 determines the received input includes a value for the element of patient data based on the type of monitoring device 104 and/or based on the content of the received input. For example, where monitoring device 104 is a heart-rate monitoring device, patient modeling server 101 recognizes the data as being a heart rate for patient 102, and associates or otherwise stores the received heart rate data with a node representing the patient's heart rate. In another example, the content of the received input includes an attribute identifier for one or more data values and patient modeling server 101 uses the attribute identifier to map the one or more data values to the corresponding node(s) representing the attributes.

In one embodiment, patient modeling server 101 determines relationships between nodes in the ontological data structure (e.g., by proceeding with method 500 at block 505 via off-page connector A).

At block 425, patient modeling server 101 compares the value from the received input with a threshold value based on the individualized range of values. In one embodiment, patient modeling server 101 retrieves the threshold value from a memory or database location associated with the node.

At block 430, patient modeling server 101 determines whether the received input satisfies the threshold value. Patient modeling server 101 determines whether the received input is within the individualized range of values for the element of patient data represented by the node. Alternatively, patient modeling server 101 determines whether the received input is within the individualized range of values for an element of patient data represented by the node and whether the received input is also within a standard range of values for the element of patient data represented by the node. In one embodiment, patient modeling server 101 determines the standard range of values for the element of patient data represented by the node based on averaging values for a pool of patients with the same condition as the patient. In other embodiments, patient modeling server 101 determines the standard range of values for the element of patient data represented by the node based on averaging values for a pool of patients based on other similarities (e.g., age, weight range, gender, etc.). In one embodiment, failure to satisfy the threshold value includes falling below a lower threshold value of the individualized range or exceeding an upper threshold value of the individualized range. In one embodiment, the received input fails to satisfy the threshold value when the received input increases or decreases from a previous value for the element of patient data represented by the node, and the amount of the increase or decrease is greater than an established amount. For example, patient modeling server 101 retrieves a previous value for the element of patient data (e.g., the last recorded value or the recorded value at a particular point in time) and compares the value in the received input with the previous value for the element of patient data. The established amount of change that patient modeling server 101 considers within an acceptable range can be established by a setting (e.g., by a physician or specialist) or based on the standard range for the particular element of patient data.

When patient modeling server 101 determines the received input does not satisfy the threshold value, the flow proceeds to block 435. When patient modeling server 101 determines the received input satisfies the threshold value, the flow proceeds to block 445.

At block 435, when patient modeling server 101 determines that the received input does not satisfy the threshold value, patient modeling server 101 registers the failure to satisfy the threshold value as the occurrence of an event.

At block 440, patient modeling server 101 transmits a notification message indicating the occurrence of the detected event. In one embodiment, message server 120 generates the notification message and transmits the notification message to one or more of patient computing device 103, monitoring device server 105, physician computing device 107, physician server 108, specialist computing device 110, specialist server 111, and user computing devices 114. For example, patient modeling server 101 transmits the notification message directly to physician computing device 107, or via physician server 108 to physician computing device 107.

In one embodiment, patient modeling server 101 sends a notification message that includes a request for additional patient data. For example, in the occurrence of an event related to the heartrate of patient 102, patient modeling server 101 generates the notification message to include a request for more frequent heartrate data, additional heart-related patient data, and/or updated patient data for nodes having relationships with the node representing the heartrate of patient 102. In another example, patient modeling server 101 sends a notification message to specialist server 111, the notification message including a request to retrieve or obtain patient data from medical devices 112.

In one embodiment, patient modeling server 101 transmits the notification message as a query. For example, in response to detecting changes in received patient data, patient modeling server 101 transmits a query to patient 102 requesting treatment status (e.g., "Did you take medication X?," "Did you change the dosage of medication Y?," etc.).

At block 445, patient modeling server 101 modifies the individualized range for the node based on the received input. In one embodiment, patient modeling server 101 modifies the individualized range for the node by retrieving the historical values for the node and using the historical values for the node and the received input, generate an updated individualized range for the node. For example, patient modeling server 101 generates a new average value for the element of patient data represented by the node, where the individualized range for patient 102 is an established amount above and below the average value. In another example, patient modeling server 101 determines the individualized range by calculating the standard deviation using the historical values and the received input.

Figure 5:
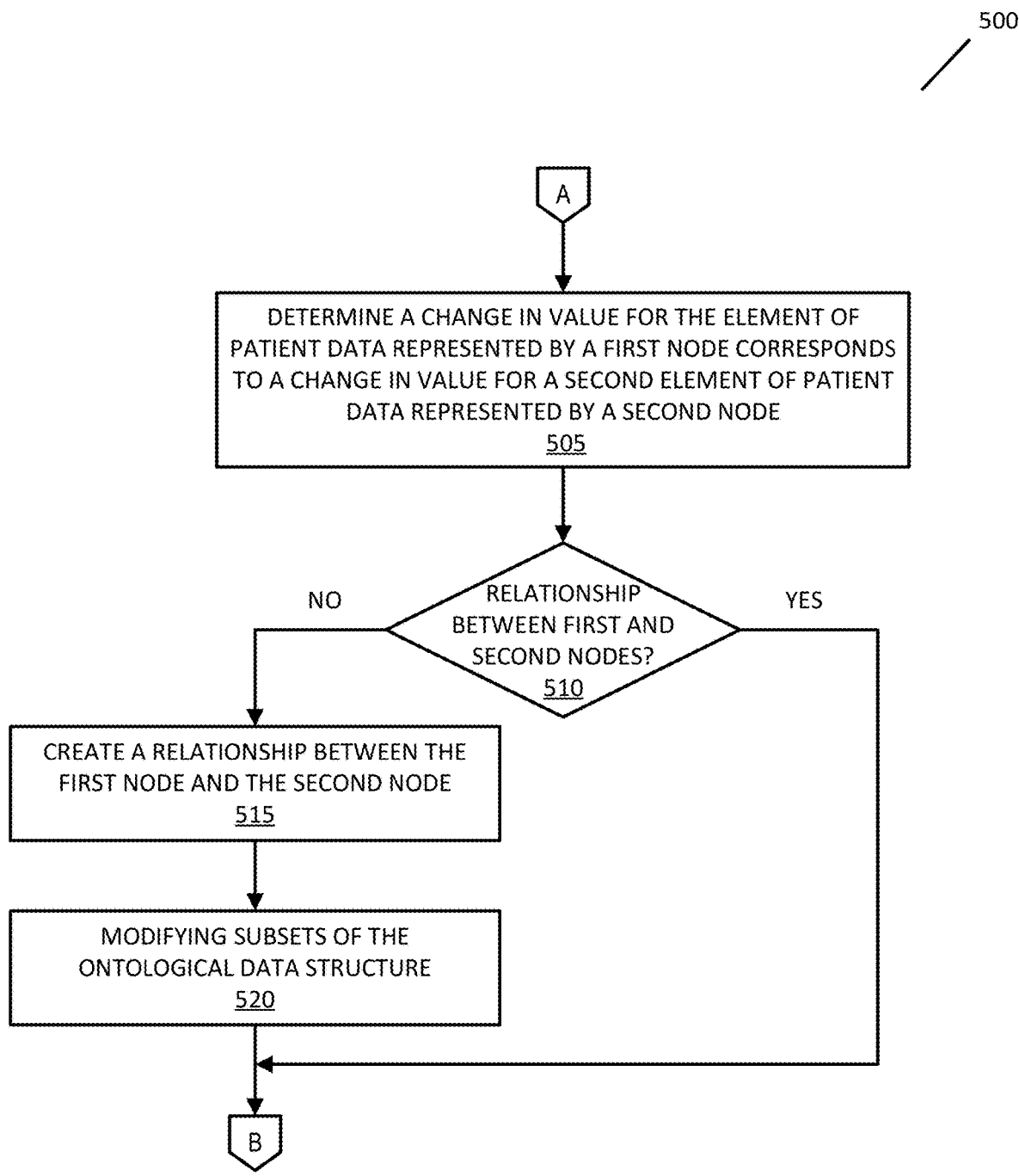
FIG. 5 is a flow chart illustrating an exemplary method of creating relationships between nodes of an ontological data structure.

FIG. 5 is a flow chart 500 illustrating an exemplary method of creating relationships between nodes of an ontological data structure.

At block 505, patient modeling server 101 determines a change in value for the element of patient data represented by a first node corresponds to a change in value for a second element of patient data represented by a second node. For example, patient modeling server 101 receives an input indicating a change in a first value for a first element of patient data represented by the first node. The input may also include a change in a second value for a second element of patient data represented by the second node. Patient modeling server 101 determines the two changes in values correspond to each other when patient modeling server 101 receives the two changes in values in the same input. For example, patient modeling server 101 receives both a systolic blood pressure value and a diastolic blood pressure value for patient 102 from monitoring device 104.

In one embodiment, patient modeling server 101 determines two changes in values correspond to each other even when patient modeling server 101 receives the two changes in values in the two different inputs if patient modeling server 101 receives the two inputs within a specified or pre-established period of time. In other embodiments, patient modeling server 101 determines the two changes in values correspond to each other in response to detecting corresponding changes between the two values multiple times or a threshold number of times. In other embodiments, patient modeling server 101 uses changes in values of inputs other than the two different inputs to detect a change. In one embodiment, patient modeling server 101 determines that changes in values for a first element of patient data influences values for a second element of patient data based on the received patient data, but not the reverse. For example, changes in levels of sodium can influence changes in blood pressure, while changes in blood pressure may not influence changes in levels of sodium.

At block 510, patient modeling server 101 determines whether a relationship exists between the first node and the second node in the ontological data structure. For example, patient modeling server 101 accesses the ontological data structure to determine if a relationship exists between the first node and the second. In one embodiment, the ontological data structure includes a relationship between the first node and the second based on known data related to the body in general that is represented in the ontological data structure by default. Alternatively, the ontological data structure includes a relationship between the first node and the second regarding patient 102 that was previously determined by patient modeling server 101. When there is an existing relationship between the first node and the second node, method 500 proceeds back to method 400 at block 425 via off-page connector B. When there is not an existing relationship between the first node and the second node, method 500 proceeds to block 515.

At block 515, patient modeling server 101 creates a relationship between the first node and the second node. In one embodiment, patient modeling server 101 creates a relationship between the first node and the second node by modifying the ontological data structure to include an edge between the first node and the second node. Alternatively, and/or additionally, patient modeling server 101 creates a pointer between the first node and the second node in a table or on the ontology itself. Patient modeling server 101 stores the new relationship in the patient models data store 136.

For example, patient 102 is diagnosed with liver cancer. As treatment for the liver cancer, specialist 109 treats patient 102 with an immunotherapy drug. As patient modeling server 101 receives patient data from various external inputs (e.g., patient computing device 103, monitoring device server 105, physician server 108, specialist server 111, etc.), patient modeling server 101 identifies changes to values of one or more other nodes representing elements of patient data. In this example, the first node represents the immunotherapy drug in the ontological data structure, and one or more second nodes represents elements of patient data (e.g., physical attributes, test results). Patient modeling server 101 correlates the introduction of the immunotherapy drug to patient 102, or changes in dosage of the immunotherapy drug, to changes in values of physical attributes or test results. For example, patient modeling server 101 may correlate the first node for the immunotherapy drug with a second node with CRP results, which indicate the amount of C-reactive protein being produced by the liver. While changes in C-reactive protein may be expected when treating for liver cancer, patient modeling server 101 also determines relationships between the immunotherapy drug and other test results (e.g., blood pressure, glucose levels, etc.). By recognizing the changes in the test results and correlating the changes to the immunotherapy drug, patient modeling server 101 identifies relationships that may be unique to patient 102 due to the specifics their condition.

In another example, patient modeling server 101 creates a relationship between a first node representing chemotherapy treatments and a second node representing medical scans of a tumor. In one embodiment, this relationship can be defined for patient 102 when the tumor is diagnosed or when chemotherapy treatments are prescribed. By recognizing the changes in tumor size using the medical scans and correlating the changes to the chemotherapy treatments, patient modeling server 101 also measures the effectiveness of treatments. In one embodiment, patient modeling server 101 automatically determines changes in tumor size by evaluating a scan history of the tumor, while in other embodiments, patient modeling server 101 parses patient data, including doctor's notations, to determine changes in tumor size.

At block 520, patient modeling server 101 modifies a subset of the ontological data structure based on the creation of the relationship between the first node and the second node. For example, patient modeling server 101 modifies subsets of the ontological data structure that include the first node to include the newly identified relationship with the second node, and further modifies subsets of the ontological data structure that include the second node to include the newly identified relationship with the first node. In one embodiment, patient modeling server 101 modifies the nodes in the subset of the ontological data structure, which can affect a graphical depiction of a filtered view of the ontological data structure, the display of which is described in FIG. 6.

In one embodiment, patient modeling server 101 generates and transmits a notification message to physicians 106, specialists 109, and additional users 113 to indicate the new relationship was determined. For example, in response patient modeling server 101 determining the new relationship for patient 102, patient modeling server 101 informs other patients with similar conditions to patient 102 and other medical professionals treating similar conditions. In other embodiments, patient modeling server 101 sends the notification message to request additional patient data for additional users 113 to determine if similar relationships can be detected from patient data for other patients.

In one embodiment, patient modeling server 101 proceeds back to method 400 at block 425 via off-page connector B.

Figure 6:
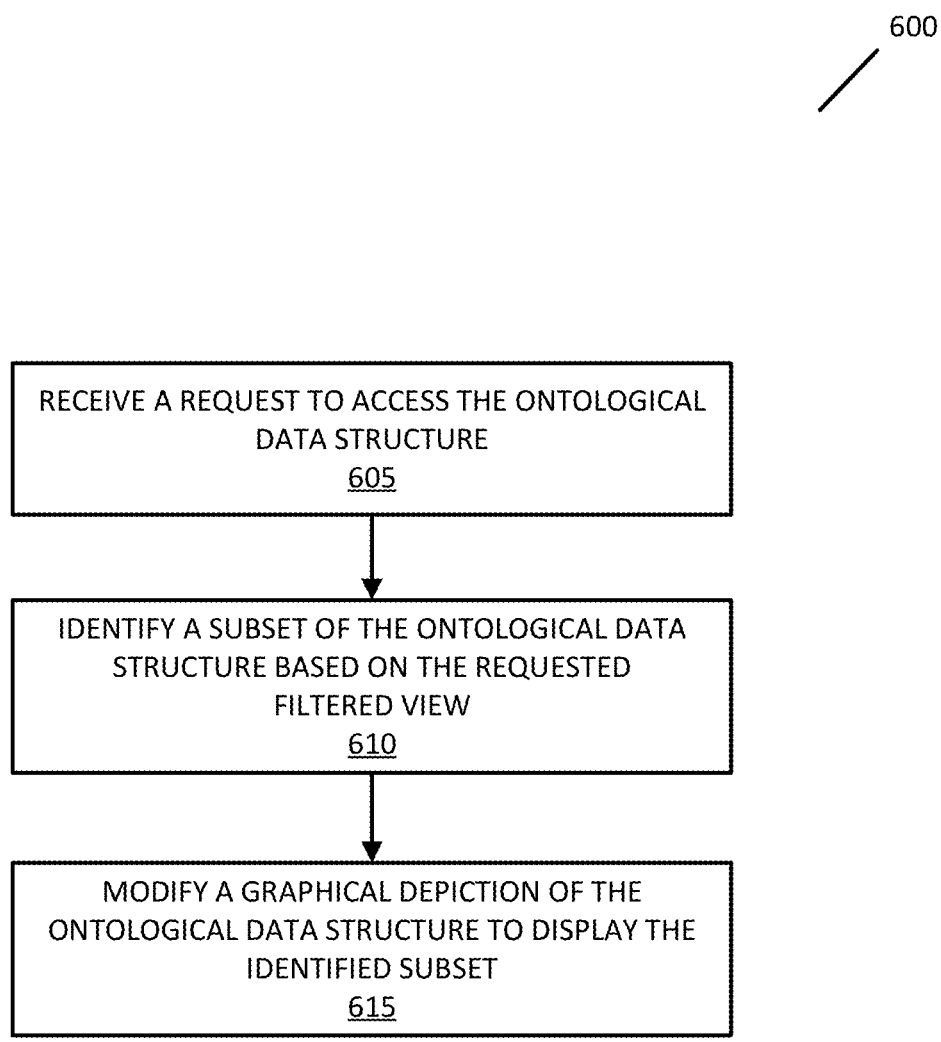
FIG. 6 is a flow chart illustrating an exemplary method of modifying an ontological data structure to present a filtered view.

FIG. 6 is a flow chart 600 illustrating an exemplary method of modifying an ontological data structure to present a filtered view.

At block 605, patient modeling server 101 receives a request to access the ontological data structure. For example, patient modeling server 101 receives the request from one of patient computing device 103, physician computing device 107, specialist computing device 110, and user computing devices 114. In one embodiment, patient modeling server 101 determines that the received request includes an indication that the requestor is requesting to view a specific subset of the nodes of the ontological data structure. For example, the requestor can request a specific subset based on a specific physical attribute (e.g., all patient data related to the liver), a specific treatment or medication, or a specific test.

In one embodiment, the specific subset of the ontological data structure can be based on a specific condition of patient 102. In one embodiment, patient profiles data store 134 includes a conditions table. Patient modeling server 101 uses the conditions table to map one or more test component identifiers to each of a plurality of conditions associated with patient 102. For example, a first column of the conditions mapping table for patient 102 indicates the conditions associated with patient 102, with a second column indicating the test component identifiers associated with the corresponding condition. In another embodiment, where the conditions table is not specific to patient 102, the conditions table includes an additional column including the patient identifier for patient 102. When patient modeling server 101 receives a request to access a specific subset of the ontological data structure for a specific condition, patient modeling server 101 accesses the conditions table to identify the test component identifiers associated with the specific condition.

In another example, the request to access the ontological data structure includes a user identifier linked to a filtered view of the ontological data structure. In one embodiment, the user identifier identifies physician 106 or specialist 109 and patient modeling server 101 determines a default filtered view associated with physician 106 or specialist 109. For example, for an oncologist treating a patient with liver cancer, patient modeling server 101 generates a filtered view of the ontological data structure, including nodes for at least: complete blood count (CBC), CMP, carcinoembryonic antigen (CEA), and C-reactive protein (CRP).

In another embodiment, a user (e.g., physician 106) selects a selectable option in a menu or other graphical user interface displayed on their computing device (e.g., physician computing device 107) to view a particular filtered view linked to the selectable option. For example, where patient 102 has a plurality of conditions, the menu includes a selectable option for a default view and one or more filtered views for each condition of the plurality of conditions. In other examples, the menu includes filtered views for general regions of the body (e.g., head, chest, lower arm), layers of the body (e.g., skin, muscular, skeletal), and for specific tests (e.g., CMP values for alkaline phosphatase (ALP), aspartate aminotransferase (AST), and alanine aminotransferase (ALT)). In one embodiment, patient modeling server 101 allows users to create custom filtered views by selecting nodes to include in the custom filtered views.

At block 610, patient modeling server 101 identifies a subset of the ontological data structure based on the requested filtered view. For example, in response to determining the user identifier associated with the request or in response to detecting a filtered view selection, patient modeling server 101 identifies the nodes associated with the requested filtered view in patient models 136. In one embodiment, patient modeling server 101 maintains a list, table, or other data structure, which includes the nodes and corresponding relationships between nodes for each filtered view. The specific subset of nodes can be unique to each filtered view, with different filtered views having overlapping nodes. For example, patient modeling server 101 identifies the subset of the ontological data structure from a conditions table when the requested filtered view is for a specific condition.

At block 615, after patient modeling server 101 identifies the subset of the ontological data structure for the requested filtered view, patient modeling server 101 modifies the graphical and data depiction of the ontological data structure to display the identified subset. In one embodiment, patient modeling server 101 maintains updated filtered views of the ontological data structure in patient models 136. In one embodiment, patient modeling server 101 generates a new or updated filtered view that includes the identified subset of nodes in response to receiving the request to access the ontological data structure. For example, patient modeling server 101 adds nodes or removes nodes to provide the requested filtered view. In one embodiment, patient modeling server 101 depicts only the nodes in the identified subset in the filtered view, greys out any additional nodes, or otherwise indicates the additional nodes as not being a part of the filtered view.

An article of manufacture may be used to store program code providing at least some of the functionality of the embodiments described above. Additionally, an article of manufacture may be used to store program code created using at least some of the functionality of the embodiments described above. An article of manufacture that stores program code may be embodied as, but is not limited to, one or more memories (e.g., one or more flash memories, random access memories—static, dynamic, or other, etc.), optical disks, CD-ROMs, DVD-ROMs, EPROMs, EEPROMs, magnetic or optical cards or other type of non-transitory machine-readable media suitable for storing electronic instructions. Additionally, embodiments of the invention may be implemented in, but not limited to, hardware or firmware utilizing an FPGA, ASIC, a processor, a computer, or a computer system including a network. Modules and components of hardware or software implementations can be divided or combined without significantly altering embodiments of the invention.

In the foregoing specification, the invention has been described with reference to specific exemplary embodiments thereof. Various embodiments and aspects of the invention(s) are described with reference to details discussed in this document, and the accompanying drawings illustrate the various embodiments. The description above and drawings are illustrative of the invention and are not to be construed as limiting the invention. References in the specification to "one embodiment," "an embodiment," "an exemplary embodiment," etc., indicate that the embodiment described may include a particular feature, structure, or characteristic, but not every embodiment may necessarily include the particular feature, structure, or characteristic. Moreover, such phrases are not necessarily referring to the same embodiment. Furthermore, when a particular feature, structure, or characteristic is described in connection with an embodiment, such feature, structure, or characteristic may be implemented in connection with other embodiments whether or not explicitly described. Additionally, as used in this document, the term "exemplary" refers to embodiments that serve as simply an example or illustration. The use of exemplary should not be construed as an indication of preferred examples. Blocks with dashed borders (e.g., large dashes, small dashes, dot-dash, and dots) are used to illustrate optional operations that add additional features to embodiments of the invention. However, such notation should not be taken to mean that these are the only options or optional operations, and/or that blocks with solid borders are not optional in some embodiments of the invention. Numerous specific details are described to provide a thorough understanding of various embodiments of the present invention. However, in certain instances, well-known or conventional details are not described in order to provide a concise discussion of embodiments of the present inventions.

It will be evident that various modifications may be made thereto without departing from the broader spirit and scope of the invention as set forth in the following claims. For example, the methods described in this document may be performed with fewer or more features/blocks or the features/blocks may be performed in differing orders. Additionally, the methods described in this document may be repeated or performed in parallel with one another or in parallel with different instances of the same or similar methods.

What is claimed is:

1. A computer-implemented method, comprising:
generating an ontological data structure having a plurality of nodes, each of the plurality of nodes associated with an element of patient data for a first patient, the ontological data structure maintaining relationships between the nodes and values for elements of patient data represented by the nodes;
determining an individualized range of values for a first element of patient data represented by a first node within the plurality of nodes based on a history of values for the first element of patient data for the first patient, the individualized range of values having a minimum value and a maximum value;
receiving an input from an external device;
determining, based on the external device or content of the received input, the received input includes a value for the first element of patient data represented by the first node within the plurality of nodes;
modifying the individualized range of values for the first element of patient data represented by the first node based on the received input;
receiving additional input from the external device;
determining, based on the external device or content of the received additional input, the additional input includes a value for the first element of patient data represented by the first node within the plurality of nodes;
comparing the value from the additional input with a threshold value, the threshold value based on the modified individualized range of values;
registering an occurrence of an event in response to determining the additional input fails to satisfy the threshold value; and
transmitting a notification message indicating the occurrence of the event.

2. The computer-implemented method of claim 1, wherein determining the received input includes the value for the first element of patient data represented by the first node within the plurality of nodes comprises:
identifying an attribute identifier associated with the value in the received input; and
mapping the received input to the first node within the plurality of nodes identified by the attribute identifier.

3. The computer-implemented method of claim 1, wherein determining the received input fails to satisfy the threshold value comprises:
determining that the received input is not within the individualized range of values for the first element of patient data represented by the first node.

4. The computer-implemented method of claim 1, wherein determining the received input fails to satisfy the threshold value comprises:
determining that the received input is not within the individualized range of values for the first element of patient data represented by the first node and is not within a standard range of values for the first element of patient data represented by the first node, the standard range of values determined based on averaging values for a pool of patients with a condition.

5. The computer-implemented method of claim 1, further comprising:
receiving a second input, the received second input including a second value for a second element of patient data represented by a second node within the plurality of nodes, the second node having a relationship with the first node;
determining the received second input indicates a change in the second value for the second element of patient data represented by the second node; and
associating the change in the second value with the occurrence of the event.

6. The computer-implemented method of claim 1, further comprising:
receiving a request to access the ontological data structure, the request including a user identifier, the user identifier linked to a filtered view of the ontological data structure, the filtered view based on a condition associated with the first patient represented by the ontological data structure;
identifying a subset of the ontological data structure based on the filtered view; and
modifying a graphical depiction of the ontological data structure to display the identified subset of the ontological data structure in response to the request.

7. The computer-implemented method of claim 6, further comprising:
determining that the first element of patient data represented by the first node has a relationship with a second element of patient data represented by a second node in response to determining that a change in the value for the first element of patient data represented by the first node corresponds to a change in a value for the second element of patient data represented by the second node;
creating the relationship between the first node and the second node in the ontological data structure; and
modifying the subset of the ontological data structure to include the second node.

8. The computer-implemented method of claim 7, wherein the first node represents an immunotherapy treatment applied to the first patient, and the second node represents a test result of the first patient.

9. The computer-implemented method of claim 1, further comprising
retrieving a second ontological data structure for a second patient, the second patient having a condition associated with the first patient represented by the ontological data structure;
determining the second ontological data structure includes an additional relationship in addition to the relationships of the ontological data structure, the additional relationship associated with an additional input;
transmitting a request for the additional input based on the additional relationship; and
modifying the ontological data structure to include the additional relationship.

10. The computer-implemented method of claim 1, wherein the first element of patient data represented by the first node is one of: a physical attribute of the first patient, a test result of the first patient, a measured data of the first patient, and/or a treatment applied to the first patient.

11. A non-transitory computer-readable medium storing instructions, which when executed by a processing device, cause the processing device to perform a method comprising:

generating an ontological data structure having a plurality of nodes, each of the plurality of nodes associated with an element of patient data for a first patient, the ontological data structure maintaining relationships between the nodes and values for elements of patient data represented by the nodes;

determining an individualized range of values for a first element of patient data represented by a first node within the plurality of nodes based on a history of values for the first element of patient data for the first patient, the individualized range of values having a minimum value and a maximum value;

receiving an input from an external device;

determining, based on the external device or content of the received input, the received input includes a value for the first element of patient data represented by the first node within the plurality of nodes;

modifying the individualized range of values for the first element of patient data represented by the first node based on the received input;

receiving additional input from the external device;

determining, based on the external device or content of the received additional input, the additional input includes a value for the first element of patient data represented by the first node within the plurality of nodes;

comparing the value from the additional input with a threshold value, the threshold value based on the modified individualized range of values;

registering an occurrence of an event in response to determining the additional input fails to satisfy the threshold value; and transmitting a notification message indicating the occurrence of the event.

12. The non-transitory computer-readable medium of claim 11, wherein determining the received input includes the value for the first element of patient data represented by the first node within the plurality of nodes comprises:
identifying an attribute identifier associated with the value in the received input; and
mapping the received input to the first node within the plurality of nodes identified by the attribute identifier.

13. The non-transitory computer-readable medium of claim 11, wherein determining the received input fails to satisfy the threshold value comprises:
determining that the received input is not within the individualized range of values for the first element of patient data represented by the first node.

14. The non-transitory computer-readable medium of claim 11, wherein determining the received input fails to satisfy the threshold value comprises:
determining that the received input is not within the individualized range of values for the first element of patient data represented by the first node and is not within a standard range of values for the first element of patient data represented by the first node, the standard range of values determined based on averaging values for a pool of patients with a condition.

15. The non-transitory computer-readable medium of claim 11, further comprising:
receiving a second input, the received second input including a second value for a second element of patient data represented by a second node within the plurality of nodes, the second node having a relationship with the first node;

determining the received second input indicates a change in the second value for the second element of patient data represented by the second node; and
associating the change in the second value with the occurrence of the event.

16. The non-transitory computer-readable medium of claim 11, further comprising:
receiving a request to access the ontological data structure, the request including a user identifier, the user identifier linked to a filtered view of the ontological data structure, the filtered view based on a condition associated with the first patient represented by the ontological data structure;
identifying a subset of the ontological data structure based on the filtered view; and
modifying a graphical depiction of the ontological data structure to display the identified subset of the ontological data structure in response to the request.

17. The non-transitory computer-readable medium of claim 16, further comprising:
determining that the first element of patient data represented by the first node has a relationship with a second element of patient data represented by a second node in response to determining that a change in the value for the first element of patient data represented by the first node corresponds to a change in a value for the second element of patient data represented by the second node;
creating the relationship between the first node and the second node in the ontological data structure; and
modifying the subset of the ontological data structure to include the second node.

18. The non-transitory computer-readable medium of claim 17, wherein the first node represents an immunotherapy treatment applied to the first patient, and the second node represents a test result of the first patient.

19. The non-transitory computer-readable medium of claim 11, further comprising:
retrieving a second ontological data structure for a second patient, the second patient having a condition associated with the first patient represented by the ontological data structure;
determining the second ontological data structure includes an additional relationship in addition to the relationships of the ontological data structure, the additional relationship associated with an additional input;
transmitting a request for the additional input based on the additional relationship; and
modifying the ontological data structure to include the additional relationship.

20. An apparatus comprising:
a processing device; and
a memory coupled to the processing device, the memory storing instructions which, when executed by the processing device, cause the apparatus to:
generate an ontological data structure having a plurality of nodes, each of the plurality of nodes associated with an element of patient data for a first patient, the ontological data structure maintaining relationships between the nodes and values for elements of patient data represented by the nodes;
determine an individualized range of values for a first element of patient data represented by a first node within the plurality of nodes based on a history of values for the first element of patient data for the first patient, the individualized range of values having a minimum value and a maximum value;
receive an input from an external device;

determine, based on the external device or content of the received input, the received input includes a value for the first element of patient data represented by the first node within the plurality of nodes;

modify the individualized range of values for the first element of patient data represented by the first node based on the received input;

receive additional input from the external device;

determine, based on the external device or content of the received additional input, the additional input includes a value for the first element of patient data represented by the first node within the plurality of nodes;

compare the value from the additional input with a threshold value, the threshold value based on the modified individualized range of values;

register an occurrence of an event in response to determining the additional input fails to satisfy the threshold value; and transmit a notification message indicating the occurrence of the event.

* * * * *